United States Patent [19]

Jessel, Jr.

[11] Plant 5,234

[45] May 22, 1984

[54] CHRYSANTHEMUM PLANT

[75] Inventor: Walter H. Jessel, Jr., Fremont, Calif.

[73] Assignee: California-Florida Plant Corporation, Fremont, Calif.

[21] Appl. No.: 366,835

[22] Filed: Apr. 9, 1982

[51] Int. Cl.[3] ..... A01H 5/00

[52] U.S. Cl. ..... Plt./74

[58] Field of Search ..... Plt./74

*Primary Examiner*—Robert E. Bagwill

*Attorney, Agent, or Firm*—James R. Cypher

[57] ABSTRACT

The present invention relates to a new distinctive cultivar of Chrysanthemum plant, named California Marble, a sport of Florida Marble, distinguished from its parent, as well as the other varieties of Yellow Marbles known to me, by its darker yellow flower color, its resistance to color fading, and fresher flower appearance during maturation. Among the Yellow Marbles, the new cultivar is most similar to its parent Florida Marble.

1 Drawing Figure

BACKGROUND OF THE INVENTION

This invention relates to a new and distinct variety of chrysanthemum plant which is a sport of the cultivar Florida Marble, U.S. Plant Pat. No. 3,288 named California Marble.

This sport was discovered and selected from a flowering of Florida Marble in commerical greenhouses in Fremont, Calif. in May 1979 because of its distinctly darker, pleasing color.

In comparison with other Marble cultivars in the yellow category, the dark sport is closest in characteristics to its parent, Florida Marble. The dark sport is similar to Florida Marble in:

1. Nine week response time.
2. Flowering height.
3. Foliage color and shape.
4. Daisy Flower Form.

The characteristics which distinguish it from its parent and the other yellow Marbles are:

1. It has a darker flower color.
2. It is less prone to color fading, and
3. There is less twisting and reflexing of the ray florets during maturity, contributing to an overall appearance of a fresher flower.

A comparison of the color and fading of the new cultivar with Yellow Marble, Polished Marble, and Florida Marble follows:

Yellow Marble: Its tonality is light yellow which fades considerably and unevenly during high temperature periods, contributing to an uneven appearance of color.

Polished Marble: Its tonality is light cream-yellow and its overall appearance is that of a pastel, very smooth color. The color fades during high temperature periods, but color is less variable than Yellow Marble.

Florida Marble: Its tonality is dark yellow and the new cultivar is closest in intensity of color to Florida Marble. The color of Florida Marble fades during high temperature periods giving an uneven appearance. The color of Florida Marble during high temperature periods, closely resembles the low temperature color of Yellow Marble.

California Marble: Its tonality is dark golden yellow. During high temperature periods the color fades less than the other Yellow Marbles described, and the overall appearance of the color is smoother and more uniform. An additional feature of California Marble is that as the flowers mature, there is less twisting and reflexing of the ray florets contributing to an overall appearance of a fresher flower, or more "tidy", as the English would describe it.

Asexual reproduction and flowerings of this new cultivar by cuttings was performed at Fremont, Calif. in commercial greenhouses. The new cultivar was found to retain its distinctive characteristics as listed herein through successive propagations.

BRIEF DESCRIPTION OF THE DRAWING

The accompanying color photographs disclose all the distinctive characteristics of the plant capable of visual representation. The photograph of the flowers in the clay pot depict the true color of the flowers, while the photograph of the plant illustrates the overall appearance and form of the plant, as well as the true color of the foliage, but the color of the flowers is not as true.

DETAILED DESCRIPTION OF THE DRAWING

The following is a detailed description of the new chrysanthemum plant of the present invention. The color terminology used in the following is in accordance with The Royal Horticultural Society Colour Chart.

The parentage of the new chrysanthemum plant is as follows: Sport of U.S. Plant Pat. No. 3,288, Florida Marble.

The classification of the new variety is as follows:

*Botanical.—Chrysanthemum morifolium, Ramat.*
*Commercial.*—Standard spray.

The following detailed botanical description is based on observations of plants grown inside commerical greenhouses at Fremont, Calif.

The height of plant and flower and foliage size established as an average using standard commercial cultural practices and the recommended treatment of long day control as known in the industry: three to four weeks long days before initiation of short days. The data provided, accurately characterizes the sport in question. Color designation and other values stated may deviate slightly from the stated values from flowering to flowering, but the deviations will be within the range expected from varying environmental, seasonal, and cultural conditions. The form of the plant is Herbaceous and it grows in an upright branching manner. The following table compares the new cultivar with its parent Florida Marble.

TABLE OF COMPARISON

| | New Cultivar (California Marble) | Florida Marble |
|---|---|---|
| PLANT: | | |
| Height | 104 cm | Same |
| Response | 9 weeks | Same |
| FOLIAGE: | | |
| Color - Upper side | 137 B–C | Same |
| Lower side | 139 C–D | Same |
| Size: | Length 12.8 cm × 8.4 cm width | Same |
| Quantity | Numerous | Same |
| Shape | Obvate lobed | Same |
| Texture | Smooth | Same |
| Ribs and Veins | Prominent | Same |
| Margins | Deeply lobed | Same |
| Serration | Prominent | Same |
| BLOOM: | | |
| Size | 8.8 cm | 9.0 cm |
| Borne | Compound lateral clusters of 5–8 flowers | Same |
| Stem Strength | Wiry | Same |
| Form | Daisy | Same |
| Color: | | |
| Center | 12A with 142A center | Same |
| Upper side | 5B | 5C |

TABLE OF COMPARISON-continued

| | New Cultivar (California Marble) | Florida Marble |
|---|---|---|
| Lower Side | 4B | 4 B–C |
| Tonality | 5 A–B | 5 B–C |
| PETALS: | | |
| Texture | Smooth | Same |
| Appearance and Form | Open at base, broad at mid-point tapering to a rounded point | Same |
| Arrangement | Composite, whorled on a single receptacle | Same |
| Persistence | Resists shattering | Same |
| Fragrance | Typical chrysanthemum | Same |
| REPRODUCTION ORGANS: | | |
| Stamen | 250 | Same |
| Pollen | None to abundant | Same |
| Arrangement | Clustered in center of flower | Same |
| Styles | Present in both ray & disc florets | Same |
| Length | Short | Same |
| Ovaries | At base of petal attached to receptacle | Same |

I claim:

1. A new and distinctive cultivar of chrysanthemum plant, substantially as herein described, and distinguished from its parent by a darker flower color, less prone to color fading, and less twisting and reflexing of the ray florets during maturation, giving the appearance of a fresher flower.

* * * * *

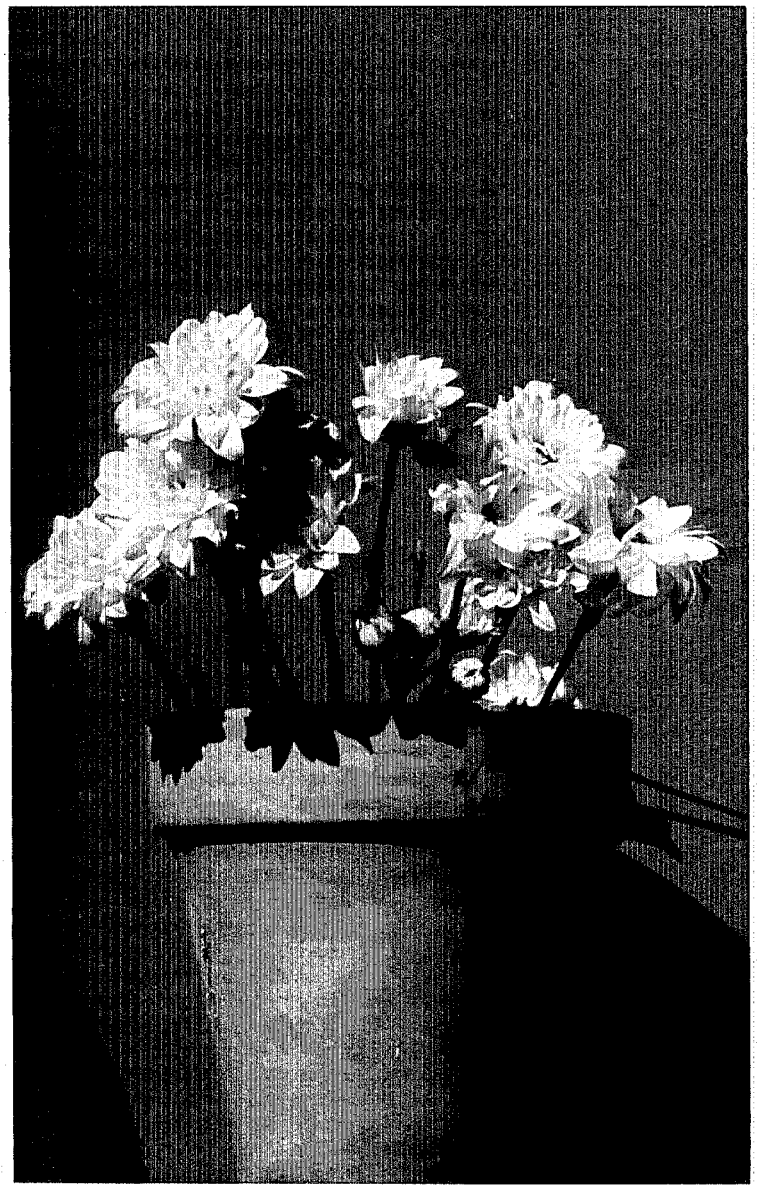

UNITED STATES PATENT AND TRADEMARK OFFICE

CERTIFICATE OF CORRECTION

PATENT NO. : Plant 5,234

DATED : May 22, 1984

INVENTOR(S) : Walter H. Jessel, Jr.

It is certified that error appears in the above–identified patent and that said Letters Patent are hereby corrected as shown below:

In Column 2, line 15, after the words "true color of the flowers" delete the comma and add a period and delete the remainder of the sentence.

Signed and Sealed this

*Seventh* Day of *May 1985*

[SEAL]

*Attest:*

DONALD J. QUIGG

*Attesting Officer* *Acting Commissioner of Patents and Trademarks*